United States Patent [19]

Das et al.

[11] Patent Number: 4,474,804
[45] Date of Patent: Oct. 2, 1984

[54] 7-OXABICYCLO SUBSTITUTED PROSTAGLANDIN PHENYL CARBOXYLIC ACID DERIVATIVES USEFUL AS CARDIOVASCULAR AGENTS

[75] Inventors: Jagabandhu Das, Plainsboro; Martin F. Haslanger, Lambertville, both of N.J.

[73] Assignee: E. R. Squibb & Sons, Inc., Princeton, N.J.

[21] Appl. No.: 533,461

[22] Filed: Sep. 19, 1983

[51] Int. Cl.$^3$ .................. A61K 31/557; C07D 307/93
[52] U.S. Cl. .................................... 424/285; 549/463
[58] Field of Search .................. 542/454, 469, 429; 424/285

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS

0043292  8/1982  European Pat. Off. .
2039909  8/1980  United Kingdom .

*Primary Examiner*—Nicky Chan
*Attorney, Agent, or Firm*—Lawrence S. Levinson; Burton Rodney

[57] ABSTRACT

7-Oxabicyclo substituted prostaglandin phenyl carboxylic acid derivatives are provided having the structural formula

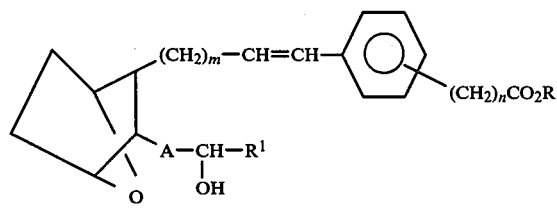

and including all stereoisomers thereof.

The compounds are cardiovascular agents useful, for example, in the treatment of thrombolytic disease.

13 Claims, No Drawings

7-OXABICYCLO SUBSTITUTED PROSTAGLANDIN PHENYL CARBOXYLIC ACID DERIVATIVES USEFUL AS CARDIOVASCULAR AGENTS

DESCRIPTION OF THE INVENTION

The present invention relates to 7-oxabicyclo substituted prostaglandin phenyl carboxylic acid derivatives which are cardiovascular agents useful, for example, in the treatment of thrombolytic disease. These compounds having the structural formula

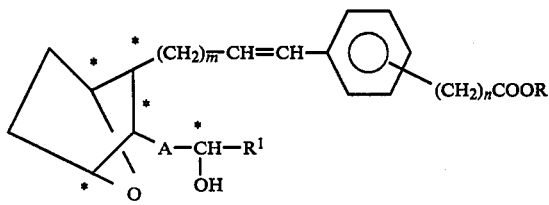

and including all stereoisomers thereof, wherein
R is H, lower alkyl or alkali metal:
A is —CH=CH—, or $(CH_2)_2$:
$R^1$ is lower alkyl, aryl-lower alkyl, aryl, cycloalkyl or cycloalkylalkyl:
m is 0 or 1 and n is 0 or 1.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aryloxy" includes any of the above lower alkyl or alkyl groups or aryl groups linked to an oxygen atom.

Preferred are those compounds of formula I wherein R is H or methyl, m is 1, n is 0, A is —CH=CH—, and $R^1$ is $(CH_2)_z CH_3$ (z is 2 to 4), $CH_2C_6H_5$,

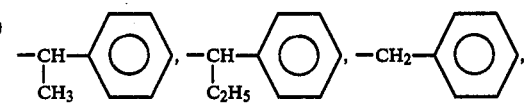

cycloalkyl, especially cyclohexyl, 1-methylcyclohexyl, cycloalkylalkyl,

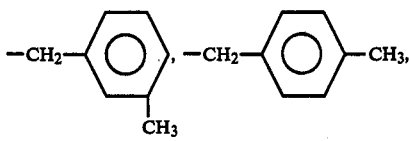

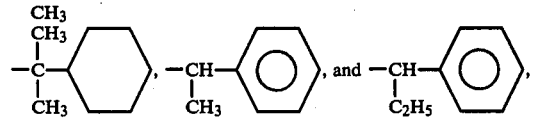

and the $COOR^1$ group
is in the meta- or para-position.

Compounds of formula I may be prepared according to the following reaction description.

(Exo)Octahydro-5,8-epoxy-1H-benzopyran-3-ol or (exo)octahydro-4,7-epoxyisobenzofuran-1-ol (prepared as described in U.S. Pat. No. 4,143,054) of the strucutre

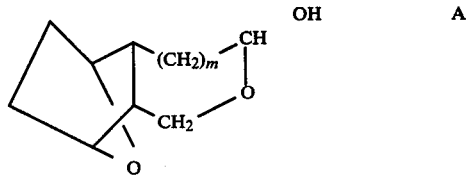

is subjected to a Wittig reaction with a carboalkoxybenzyl phosphonium bromide

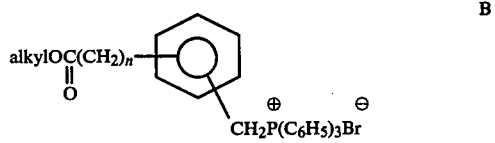

to form a mixture of the cis and trans olefins

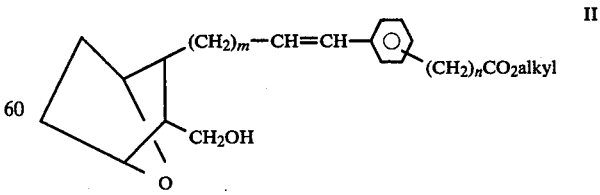

which isomers may be separated by column chromatography or other conventional separation techniques into the individual cis and trans isomers or slow moving and fast moving isomers.

The cis or trans isomer of II is converted to the corresponding aldehyde by subjecting II to a Collins oxidation, for example, by reacting II with chromium trioxide in a basic organic solvent, such as pyridine, to form aldehyde III

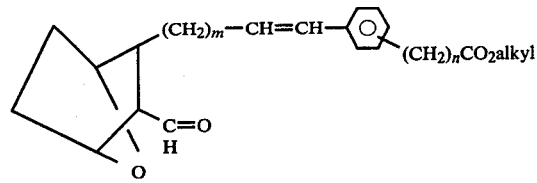

III

Aldehyde III is then reacted with phosphonate C

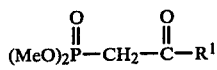

C employing a molar ratio of III:C of within the range of from about 1:1 to about 0.5:1 under basic conditions, such as in the presence of sodium hydride or lithium diisopropylamine and an inert solvent, such as dimethoxyether (DME), ether, tetrahydrofuran or toluene to form compound IV

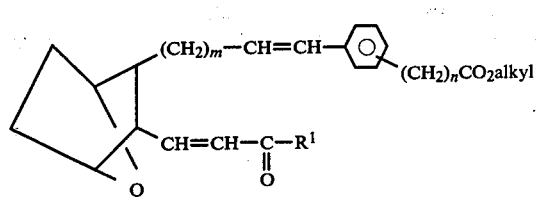

IV

Compound IV is then reduced employing a reducing agent such as sodium borohydride or sodium cyanoborohydride in the presence of cesium chloride and a solvent such as methanol or methanol/tetrahydrofuran to form a mixture of slow moving and fast moving alcohol ester isomers V

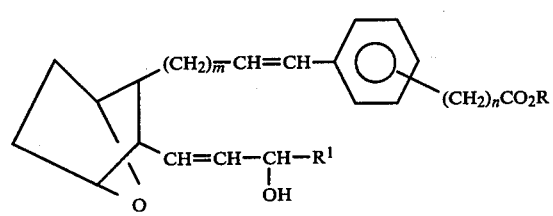

V (mixture of slow moving and fast moving isomers)

The isomers represented by structure V are separated by column chromatography or other conventional means and the desired isomer is then hydrolyzed, for example, by reaction with sodium hydroxide, potassium hydroxide or lithium hydroxide to form the corresponding alkali metal salt which is treated with acid such as HCl or oxalic acid to form the corresponding acid VI

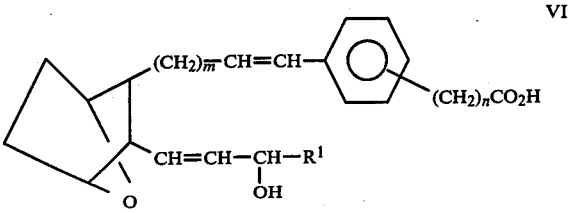

VI

Compounds of formula I wherein A is $(CH_2)_2$ are prepared by reducing compound IV using as the reducing agent sodium borohydride in a basic solvent like pyridine, triethylamine, piperidine, collidine or diethylaniline to form the ester VA

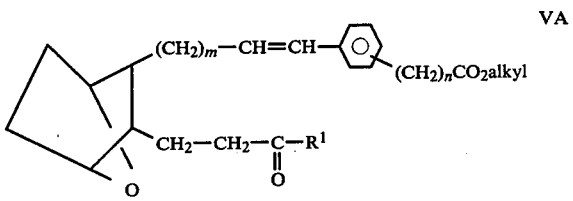

VA

The ester VA may reduced by reaction with sodium borohydride or sodium cyanoborohydride as described above with respect to compound IV to form the corresponding alcohol ester which may then be hydrolyzed to the corresponding acid VIA by reacting VA with sodium hydroxide, potassium hydroxide or lithium hydroxide to form the corresponding alkali metal salt which is neutralized by treatment with acid such as HCl or oxalic acid to form VIA

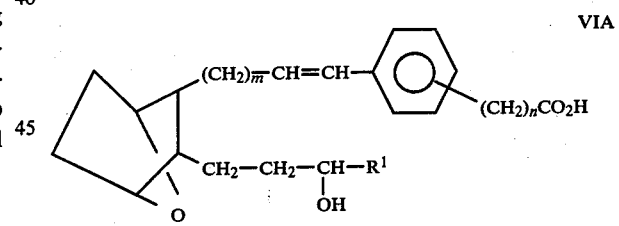

VIA

The compounds of this invention have five centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the formula I compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

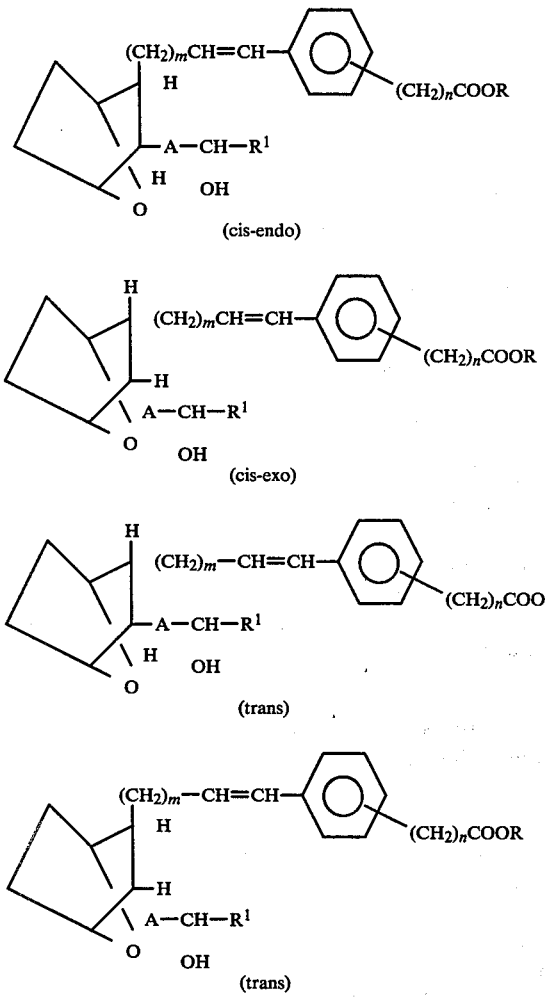

The wavy ( ) line in the above formulae indicates that the hydroxy group in each of the compounds of formulae Ia-Id is either R(β) or S(α).

The nucleus in each of the compounds of the invention is depicted as

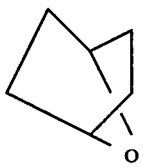

for matter of convenience; it will also be appreciated that the nucleus in the compounds of the invention may be depicted as

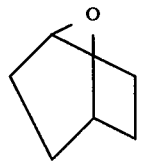

The compounds of this invention are cardiovascular agents useful as platelet aggregation inhibitors. e.g., for treatment of thrombolytic disease, such as coronary or cerebral thromboses. They are also selected thromboxane antagonists, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of this invention. All temperatures are in °C. unless otherwise indicated.

EXAMPLE 1

[(1β,2α(E),3α(1E),4β)]-3-[3-[3-(3-Cyclohexyl-3-hydroxy-1-propenyl)-7-oxabicyclo[2.2.1]hept-2-yl]-1-propenyl]benzoic acid

A.
[(1β,2α(Z),3α,4β)]-3-[3-Hydroxymethyl-7-oxabicyclo[2.2.1]hept-2-yl]-1-propenyl]-benzoic acid, methyl ester and

B.
[(1β,2α(E),3α,4β)]-3-[3-Hydroxymethyl-7-oxabicyclo[2.2.1]hept-2-yl]-1-propenyl]-benzoic acid, methyl ester A mixture of 634.8 mg of (exo)octahydro-5,8-epoxy-1H-benzopyran-3-ol (prepared as described in U.S. Pat. No. 4,143,054) (3.75 mmole), 2.273 g of 3-carbomethoxybenzyltriphenyl phosphonium bromide (4.6 mmole, 1.2 eq.) and 2.66 ml of 1.7M potassium tert-amylate solution in toluene in 15 ml of dry toluene was stirred under argon at 25° C. for 18 hours. The reaction was quenched with glacial acetic acid and poured into 300 ml of brine and extracted with three 100 ml portions of ether. The ethereal extracts were washed with two 50 ml portions of saturated sodium bicarbonate, 50 ml of 10% HCl, 50 ml of brine, dried and concentrated to yield 1.8 g of a crude oil.

This crude oil was purified on a LPS-1 silica gel column, eluting with 2 liters of 20% EtOAc/hexanes and 3 liters of 40% EtOAc/hexanes to give 130 mg of title B cis-olefin and 230 mg of title A trans-olefin.

C. [(1β,2α(E),3α,4β)]-3-[3-Formyl-7-oxabicyclo[2.2.1]hept-2-yl]-1-propenyl]-benzoic acid, methyl ester To a solution of 1.2 g pyridine (15 mmole, 12 eq.) in 30 ml of dry CH$_2$Cl$_2$ at 25° C. was added 755 mg chromium trioxide (7.5 mmole, 6 eq.). The mixture was stirred at 25° C. for 30 minutes. 5 g Celite was added, followed by a solution of 380 mg title B alcohol (1.26 mmole) in 2 ml CH$_2$Cl$_2$. The reaction mixture was stirred at 25° C. for 30 minutes then filtered through a bed of Celite. The filtrate was concentrated and the residue was taken up in 50 ml of ether. The ethereal solution was washed with two 20 ml portions of saturated NaHCO$_3$, 20 ml of 1N HCl, 20 ml of saturated NaHCO$_3$, dried, filtered through a bed of florosil, and concentrated to give the title C aldehyde.

D.
[(1β,2α(E),3α(1E),4β)]-3-[3-[3-(3-Cyclohexyl-3-oxo-1-propenyl)-7-oxabicyclo[2.2.1]hept-2-yl]-1-propenyl]-benzoic acid, methyl ester To a slurry of 66 mg of 50% sodium hydride in mineral oil (1.38 mmole, 1.1 eq) in 5 ml of dimethoxyethane (DME) at 0° C. under argon was added 442 mg of 2-oxo-2-cyclohexylethyldimethylphosphonate (1.89 mmole, 1.5 eq.). The mixture was stirred for 1 hour at 25° C. then to it was added a solution of title C aldehyde in 1 ml DME. After 1 hour stirring at 25° C. the reaction was quenched with glacial acetic acid and concentrated. The residue was taken up in 50 ml ether, washed with three 20 ml portions of saturated NaHCO$_3$, 20 ml of brine, and concentrated. The residue was purified by a simple filtration through a bed of LPS-1 silica gel with 20% ether/hexane. The filtrate was concentrated to give 340 mg of title D compound as a white solid.

E.
[(1β,2α(E),3α(1E),4β)]-3-[3-[3-(3-Cyclohexyl-3-hydroxy-1-propenyl)-7-oxabicyclo[2.2.1]hept-2-yl]-1-propenyl]-benzoic acid, methyl ester and

F.
[(1β,2α(Z),3α(1E),4β)]-3-[3-[3-(3-Cyclohexyl-3-hydroxy-1-propenyl)-7-oxabicyclo-[2.2.1]hept-2-yl]-1-propenyl]benzoic acid, methyl ester To 340 mg title D enone (0.83 mmole) in 3 ml of methanol was added 286 mg cerium trichloride (0.83 mmole, 1 eq.) at 25° C. The mixture was stirred for 10 minutes then cooled to 0° C. To this mixture at 0° C. was added slowly 31 mg sodium borohydride (0.83 mmole, 4 eq.). The reaction mixture was stirred for 10 minutes then poured into 300 ml of saturated ammonium chloride, extracted with three 50 ml portions of ether, dried and concentrated to give 340 mg of a crude oil.

Separation and purification was done on a LPS-1 silica gel column, eluting with 25% EtOAc/hexanes to give 200 mg of title F compound and 55 mg of title E compound.

TLC of title F compound: Silica gel; EtOAc/Hex (1:1); R$_f$~0.60.
TLC of title E compound: Silica gel; EtOAc/Hex (1:1); R$_f$~0.50.

G.
[(1β,2α(E),3α(1E),4β)]-3-[3-[3-(3-Cyclohexyl-3-hydroxy-1-propenyl)-7-oxabicyclo[2.2.1]hept-2-yl]-1-propenyl]-benzoic acid To a mixture of 200 mg of title E ester (0.48 mmole) in 16 ml THF and 4 ml H$_2$O was added slowly 9.7 ml of a 1M solution of potassium hydroxide (9.7 mmole, 20 eq.). The mixture was stirred for 32 hours at 50°-60° C. The cooled mixture was concentrated. The residue was diluted with 20 ml H$_2$O, acidified with saturated oxalic acid to pH 3, extracted with three 20 ml portions of ether. The combined ethereal extract was washed with two 10 ml portions of water, 10 ml of brine, dried and concentrated to give 173.6 mg title compound as a white solid. This was dried further for 2 days under high vacuum at 25° C.

TLC: Silica gel, 5% MeOH/CH$_2$Cl$_2$, R$_f$~0.45.

Anal. Calcd (includes 0.4 moles H$_2$O): C, 74.35; H, 8.18. Found: C, 74.35; H, 8.17.

EXAMPLE 2
[1β,2α(Z),3α(1E), 4β]-3-[3-[3-(3-Cyclohexyl-3-hydroxy-1-propenyl)-7-oxabicyclo[2.2.1]hept-2-yl]-1-propenyl]benzoic acid Following the procedure of Example 1, part G, except substituting [1β,2α(E),3α(1E),4β]-[3-[3-(3-(cyclohexyl-3-hydroxy-1-propenyl)-7-oxabicyclo-[2.2.1]hept-2-yl]-1-propenyl]benzoic acid, methyl ester (prepared in Example 1, part F) for the Example 1, part E ester, the title compound is obtained.

TLC: Silica gel; 5% MeOH/CH$_2$Cl$_2$; R$_f$~0.45.
Anal. Calcd (included 0.86 moles H$_2$O): C, 75.35; H, 8.24. Found: C, 75.35; H, 8.01.

EXAMPLE 3
[1β,2α(Z),3β,4β]-3-[3-[3-(3-Cyclohexyl-3-hydroxy-1-propenyl)-7-oxabicyclo[2.2.1]hept-2-yl]-1-propenyl]-benzoic acid Following the procedure of Example 1 except substituting trans-octahydro-5,8-epoxy-1H-benzopyran-3-ol for (exo)-octahydro-5,8-epoxy-1H-benzopyran-3-ol, the title compound is obtained.

EXAMPLE 4
[(1β,2α(E),3α,4β)]-3-[3-[3-(3-Cyclohexyl-3-hydroxy-1-propyl)-7-oxabicyclo[2.2.1]hept-2-yl]-1-propenyl]benzoic acid

A.
[(1β,2α(E),3α,4β)]-3-[3-[3-(3-Cyclohexyl-3-oxo-1-propyl)-7-oxabicyclo[2.2.1]hept-2-yl]-1-propenyl]benzoic acid, methyl ester To a solution of 408 mg of Example 1 title D enone (1 mmole) in 20 ml of dry pyridine is added with stirring 38 mg of sodium borohydride (1 mmole, 4 eq.). The reaction mixture is stirred at room temperature for 3 days, whereupon it is poured into 150 ml of water containing 15 ml of saturated sodium bicarbonate solution. The mixture is stirred for several minutes and is then extracted with ether. The ether extract is dried over anhydrous magnesium sulfate and concentrated in vacuo to give the title A ketone.

B.
[(1β,2α(E),3α,4β)]-3-[3-[3-(3-Cyclohexyl-3-hydroxy-1-propyl)-7-oxabicyclo[2.2.1]hept-2-yl]-1-propenyl]benzoic acid, methyl ester Following the procedure of Example 1, part F, except substituting title A ketone for [(1β,2α(E),3α,4β)]-3-[3-[3-(3-cyclohexyl-3-oxo-1-propenyl)-7-oxabicyclo-[2.2.1]hept-2-yl]-1-propenyl]benzoic acid, methyl ester, the title compound is obtained.

C.
[(1β,2α(E),3α,4β)]-3-[3-[3-(3-Cyclohexyl-3-hydroxy-1-propyl)-7-oxabicyclo[2.2.1]hept-2-yl]-1-propenyl]benzoic acid Following the procedure of Example 1, part G, except substituting title B methyl ester for [(1β,2α(E),3α,4β)]-3-[3-[3-(3-cyclohexyl-3-hydroxy-1-propenyl)-7-oxabicyclo[2.2.1]hept-2-yl]-1-propenyl]benzoic acid, methyl ester, the title acid is obtained.

EXAMPLE 5

[1β,2α(Z),3α(1E),4β]-4-[3-[3-(3-Phenyl-3-hydroxy-1-propenyl)-7-oxabicyclo[2.2.1]hept-2-yl]-1-propenyl]-benzoic acid Following the procedure of Example 1 except substituting 4-carbomethoxybenzyltriphenylphosphonium bromide for 3-carbomethoxybenzyltriphenylphosphonium bromide and substituting 2-oxo-2-phenethyldimethylphosphonate for 2-oxo-2-cyclohexylethyldimethylphosphonate, the title compound is obtained.

EXAMPLE 6

[1β,2α(Z),3α(1E),4β]-3-[3-[3-(3-Propyl-3-hydroxy-1-propenyl)-7-ocabicyclo[2.2.1]hept-2-yl]-1-propenyl]-benzoic acid Following the procedure of Example 1 except substituting 2-oxo-2-pentyldimethylphosphonate for 2-oxo-2-cyclohexylethyldimethylphosphonate, the title compound is obtained.

EXAMPLE 7

[1β,2α(Z),3α(1E),4β]-2-[3-[3-(3-Cyclohexylmethyl-3-hydroxy-1-propenyl)-7-oxabicyclo[2.2.1]hept-2-yl]-1-propenyl]benzoic acid Following the procedure of Example 1 except substituting 2-carbomethoxybenzyltriphenylphosphonium bromide for 3-carbomethoxybenzyl triphenylphosphonium bromide and substituting 2-oxo-2-cyclohexylpropyldimethylphosphonate for 2-oxo-2-cyclohexylethyldimethylphosphonate, the title compound is obtained.

EXAMPLE 8

[1β,2α(Z),3α(1E),4β]-3-[3-[3-(3-Benzyl-3-hydroxy1-propenyl)-7-oxabicyclo[2.2.1]hept-2-yl]-1-propenyl]-benzoic acid Following the procedure of Example 1 except substituting 2-oxo-2-phenylpropyldimethylphosphonate for 2-oxo-2-cyclohexylethyldimethylphosphonate, the title compound is obtained.

EXAMPLE 9

[1β,2α(Z),3α(1E),4β]-4-[3-[3-(3-Ethyl-3-hydroxy-1-propenyl)-7-oxabicyclo[2.2.1]hept-2-yl]-1-propenyl]-benzoic acid Following the procedure of Example 1 except substituting 4-carbomethoxybenzyltriphenylphosphonium bromide for 3-carbomethoxybenzyltriphenylphosphonium bromide and substituting 2-oxo-2-butyldimethylphosphonate for 2-oxo-2-cyclohexylethyldimethylphosphonate, the title compound is obtained.

EXAMPLE 10

[1β,2α(Z),3β,4β]-3-[3-[3-(p-Tolyl)-3-hydroxy-1-propenyl]-7-oxabicyclo[2.2.1]hept-2-yl]-1-propenyl]-benzoic acid Following the procedure of Example 3 except substituting 2-oxo-2-(p-tolyl)ethyldimethylphosphonate for 2-oxo-2-cyclohexylethyldimethylphosphonate, the title compound is obtained.

EXAMPLE 11

[1β,2α(Z),3β,4β]-3-[3-[3-(3-Butyl-3-hydroxy-1-propenyl)-7-oxabicyclo[2.2.1]hept-2-yl]-1-propenyl]-benzoic acid Following the procedure of Example 3 except substituting 2-oxo-2-hexyldimethylphosphonate for 2-oxo-2-cyclohexylethyldimethylphosphonate, the title compound is obtained.

EXAMPLE 12

[1β,2α(5Z)3β,4β]-4-[3-[3-(3-Cyclopentylethyl-3-hydroxy-1-propenyl)-7-oxabicyclo[2.2.1]hept-2-yl]-1-propenyl]benzoic acid Following the procedure of Example 3 except substituting 4-carbomethoxybenzyltriphenylphosphonium bromide for 3-carbomethoxybenzyltriphenylphosphonium bromide and substituting 2-oxo-2-cyclopentylbutyldimethylphosphonate for 2-oxo-2-cyclohexylethyldimethylphosphonate, the title compound is obtained.

EXAMPLE 13

[1β,2α(5Z)3β,4β]-2-[3-[3-(3-Phenethyl-3-hydroxy-1-propenyl)-7-oxabicyclo[2.2.1]hept-2-yl]-1-propenyl]-benzoic acid Following the procedure of Example 3 except substituting 2-carbomethoxybenzyltriphenylphosphonium bromide for 3-carbomethoxybenzyltriphenylphosphonium bromide and substituting 2-oxo-2-phenylbutyldimethylphosphonate for 2-oxo-2-cyclohexylethyldimethylphosphonate, the title compound is obtained.

EXAMPLE 14

[1β,2α(5Z),3β,4β]-3-[3-[3-(3-Cycloheptyl-3-hydroxy-1-propenyl)-7-oxabicyclo[2.2.1]hept-2-yl]-1-propenyl]-benzoic acid Following the procedure of Example 3 except substituting 2-oxo-2-cycloheptylethyldimethylphosphonate for 2-oxo-2-cyclohexylethyldimethylphosphonate, the title compound is obtained.

EXAMPLE 15

[1β,2α(Z),3α(1E),4β]-3-[3-[3-(3-Cyclopentyl-3-hydroxy-1-propenyl)-7-oxabicyclo[2.2.1]hept-2-yl]-1-propenyl]benzoic acid Following the procedure of Examples 4 and 1 or 2 except substituting 2-oxo-2-cyclopentylethyldimethylphosphonate for 2-oxo-2-cyclohexylethyldimethylphosphonate, the title compound is obtained.

EXAMPLE 16

[1β,2α(Z),3α(1E),4β]-4-[3-[3-(3-Phenyl-3-hydroxy-1-propenyl)-7-oxabicyclo[2.2.1]hept-2-yl]-1-propenyl]-benzoic acid Following the procedure of Examples 4 and 1 or 2 except substituting 4-carbomethoxybenzyltriphenylphosphonium bromide for 3-carbomethoxybenzyltriphenylphosphonium bromide and substituting 2-oxo-2-phenethyldimethylphosphonate for 2-oxo-2-cyclohexylethyldimethylphosphonate, the title compound is obtained.

EXAMPLE 17

[1β,2α(Z),3α(1E),4β]-3-[3-[3-(3-Methyl-3-hydroxy-1-propenyl)-7-oxabicyclo[2.2.1]hept-2-yl]-1-propenyl]-benzoic acid Following the procedure of Examples 4 and 1 or 2 except substituting 2-oxo-2-propyldimethylphsophonate for 2-oxo-2-cyclohexylethyldimethylphosphonate, the title compound is obtained.

EXAMPLE 18

[1β,2α(Z),3α(1E),4β]-2-[3-[3-(3-Benzyl-3-hydroxy-1-propenyl)-7-oxabicyclo[2.2.1]hept-2-yl]-1-propenyl]benzoic acid Following the procedure of Examples 4 and 1 or 2 except substituting 2-carbomethoxybenzyltriphenyl-phosphonium bromide for 3-carbomethoxybenzyltri-phenylphosphonium bromide and substituting 2-oxo-2-phenylpropyldimethyl-phosphonate for 2-oxo-2-cyclohexylethyldimethyl-phosphonate, the title compound is obtained.

EXAMPLE 19

[1β,2α(Z),3α(1E),4β]-3-[3-[3-(3-Cyclohexylmethyl-3-hydroxy-1-propenyl)-7-oxabicyclo[2.2.1]hept-2-yl]-1-propenyl]benzoic acid Following the procedure of Examples 4 and 1 or 2 except substituting 2-oxo-2-cyclohexylpropyldimethyl-phosphonate for 2-oxo-2-cyclohexylethyldimethylphosphonate, the title compound is obtained.

EXAMPLE 20

[(1β,2α,3α(E),4β)]-3-[3-[3-(3-Cyclohexyl-3-hydroxy-1-propenyl)-7-oxabicyclo[2.2.1]hept-2-yl]-1-vinyl]phenyl acetic acid Following the precedure of Example 1 except substituting (exo)octahydro-4,7-epoxy-isobenzofuran-1-ol for (exo)octahydro-5,8-epoxy-1H-benzopyran-3-ol and 3-carbomethoxymethyl benzyl triphenyl phosphonium bromide for 3-carbomethoxy benzyl triphenyl phosphonium bromide, the title compound is obtained.

EXAMPLE 21

[(1β,2α,3α(E),4β)]-3-[3-[3-(3-Cyclohexyl-3-hydroxy-1-propenyl)-7-oxabicyclo[2.2.1]hept-2-yl]-1-propenyl]-phenyl acetic acid Following the procedure of Example 1 except substituting 3-carbomethoxymethyl benzyl triphenyl phosphonium bromide for 3-carbomethoxy benzyl triphenylphosphonium bromide, the title compound is obtained.

EXAMPLE 22

[(1β,2α,3α(E),4β)]-3-[3-[3-(3-Cyclohexyl-3-hydroxy-1-propenyl)-7-oxabicyclo[2.2.1]hept-2-yl]-1-vinyl]benzoic acid Following the procedure of Example 1 except substituting (exo)octahydro-4,7-epoxyisobenzofuran-1-ol for (exo)octahydro-5,8-epoxy-1H-benzopyran-3-ol, the title compound is obtained.

What is claimed is:

1. A compound having the structural formula

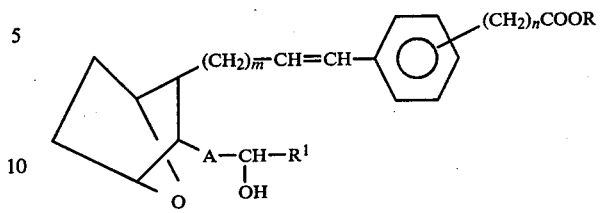

and including all stereoisomers thereof, wherein;

R is H, lower alkyl or alkali metal;

A is —CH=CH—, or (CH$_2$)$_2$;

R$^1$ is lower alkyl, aryl-lower alkyl, aryl, cycloalkyl or cycloalkylalkyl;

m is 0 or 1 and n is 0 or 1; wherein the term "aryl" used by itself or as part of another group refers to monocyclic or bicyclic aromatic groups containing from 6 to 10 carbons in the ring portion and the term "cycloalkyl" used by itself or as part of another group refers to saturated cyclic hydrocarbon groups containing 3 to 12 carbons.

2. The compound as defined in claim 1 wherein A is —CH=CH.

3. The compound as defined in claim 1 wherein R$^1$ is cycloalkyl.

4. The compound as defined in claim 1 wherein —COOR is in the meta-position.

5. The compound as defined in claim 1 wherein R is H.

6. The compound as defined in claim 1 wherein A is (CH$_2$)$_2$.

7. The compound as defined in claim 1 wherein R$^1$ is cyclohexyl, A is —CH=CH— and COOR is in the meta-position.

8. The compound as defined in claim 1 wherein m is 1 and n is 0.

9. The compound as defined in claim 1 having the name [1β,2α(Z),3α(1E),4β]-3-[3-[3-(3-cyclohexyl-3-hydroxy-1-propenyl)-7-oxabicyclo[2.2.1]hept-2-yl]-1-propenyl]benzoic acid or its methyl ester, including all isomers of each.

10. The compound as defined in claim 1 having the name [1β,2α(E),3α(1E),4β]-3-[3-[3-(3-cyclohexyl-3-hydroxy-1-propenyl)-7-oxabicyclo[2.2.1]hept-2-yl]-1-propenyl]benzoic acid or its methyl ester, including all isomers of each.

11. A method of inhibiting platelet aggregation which comprises administering to a mammalian host an effective amount of a compound as defined in claim 1 or a pharmaceutically acceptable salt thereof.

12. A composition for inhibiting platelet aggregation comprising an effective amount of a compound as defined in claim 1 or a pharmaceutically acceptable salt thereof, and a pharmaceutically acceptable carrier therefor.

13. The method as defined in claim 11 wherein said compound is administered in an amount within the range of from about 1 to about 100 mg/kg.

* * * * *

UNITED STATES PATENT AND TRADEMARK OFFICE
CERTIFICATE OF CORRECTION

PATENT NO. : 4,474,804

DATED : October 2, 1984

INVENTOR(S) : Jagabandhu Das et al.

It is certified that error appears in the above—identified patent and that said Letters Patent is hereby corrected as shown below:

Column 2, line 35, structure A should read as follows

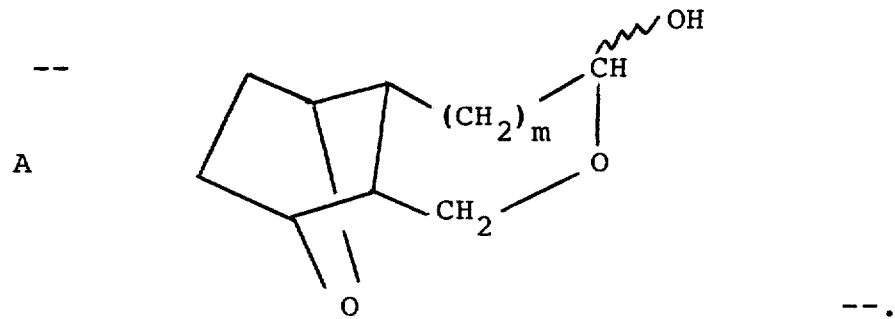

Column 5, structures Ia, Ib, Ic and Id should read as follows

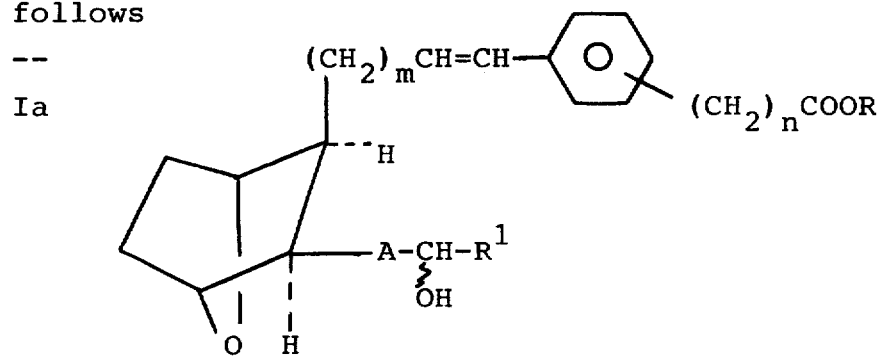

(cis-endo)

UNITED STATES PATENT AND TRADEMARK OFFICE
CERTIFICATE OF CORRECTION

PATENT NO. : 4,474,804

DATED : October 2, 1984

INVENTOR(S) : Jagabandhu Das et al.

It is certified that error appears in the above—identified patent and that said Letters Patent is hereby corrected as shown below:

Ib
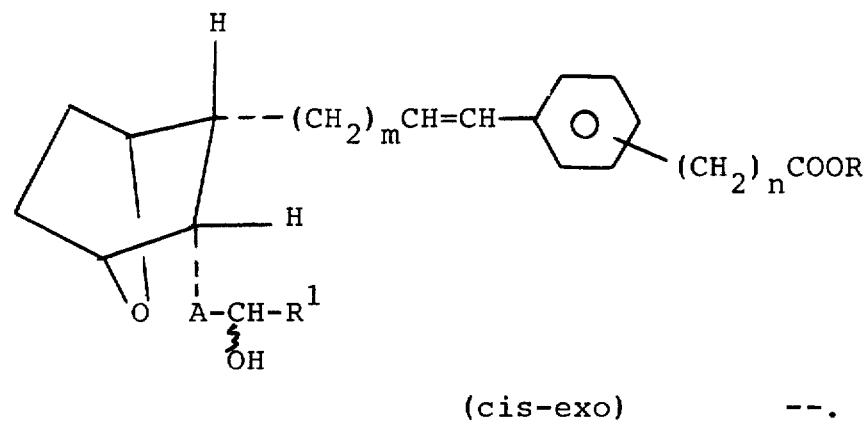
(cis-exo)

Ic
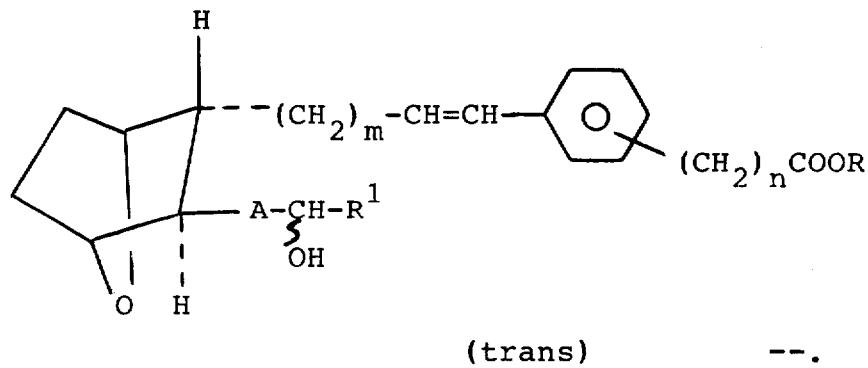
(trans)

UNITED STATES PATENT AND TRADEMARK OFFICE
CERTIFICATE OF CORRECTION

PATENT NO. : 4,474,804

DATED : October 2, 1984

INVENTOR(S) : Jagabandhu Das et al.

It is certified that error appears in the above—identified patent and that said Letters Patent is hereby corrected as shown below:

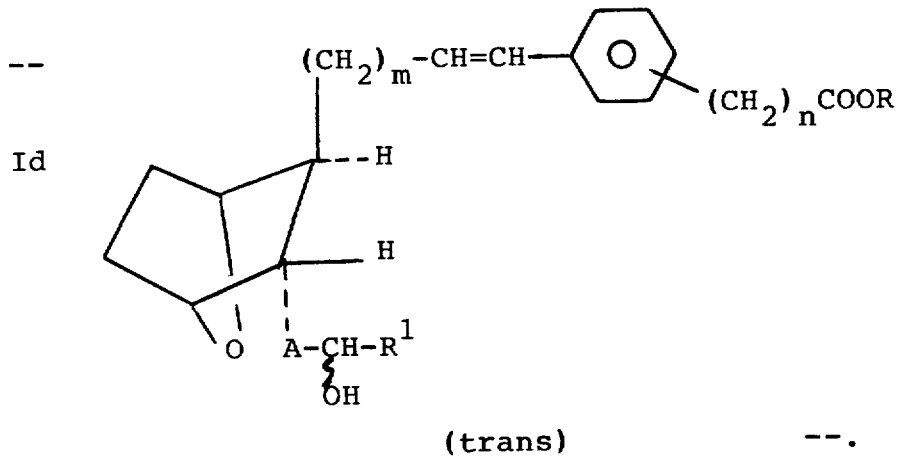

Column 5, line 41, "wavy ( )" should read --wavy ($)--.

Signed and Sealed this

Thirtieth Day of April 1985

[SEAL]

Attest:

DONALD J. QUIGG

Attesting Officer     Acting Commissioner of Patents and Trademarks